(12) United States Patent
Samproni (10) Patent No.: US 12,072,311 B2
(45) Date of Patent: Aug. 27, 2024

(54) SENSOR ASSEMBLY AND METHOD OF USING SAME

(71) Applicant: Siemens Healthcare Diagnostics Inc., Tarrytown, NY (US)

(72) Inventor: Jennifer Samproni, Braintree, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 413 days.

(21) Appl. No.: 16/762,631

(22) PCT Filed: Nov. 16, 2018

(86) PCT No.: PCT/US2018/061556
§ 371 (c)(1),
(2) Date: May 8, 2020

(87) PCT Pub. No.: WO2019/099855
PCT Pub. Date: May 23, 2019

(65) Prior Publication Data
US 2020/0278313 A1  Sep. 3, 2020

Related U.S. Application Data

(60) Provisional application No. 62/587,856, filed on Nov. 17, 2017.

(51) Int. Cl.
*G01N 27/27* (2006.01)
*G01N 21/17* (2006.01)

(52) U.S. Cl.
CPC ............. *G01N 27/27* (2013.01); *G01N 21/17* (2013.01); *G01N 2021/1734* (2013.01)

(58) Field of Classification Search
CPC .............. G01N 27/27; G01N 21/17; G01N 2021/1734; G01N 27/3272; G01N 33/492;
(Continued)

(56) References Cited

U.S. PATENT DOCUMENTS 4,911,794 A * 3/1990 Parce .................. G01N 27/327
   204/403.08
5,063,081 A * 11/1991 Cozzette ................ C12Q 1/001
   435/7.1
(Continued)

FOREIGN PATENT DOCUMENTS

AU    2011253076 A1    12/2012
CA    2954563 A1    1/2016
(Continued)

OTHER PUBLICATIONS

International Search Report and Written Opinion of International Application No. PCT/US2018/061556 dated Feb. 1, 2019.
(Continued)

*Primary Examiner* — Mohamed K Amara (57) ABSTRACT

The present disclosure describes a method in which a sample is passed through a fluid flow path of a sensor assembly such that the sample intersects at least one sensor comprising at least three electrodes arranged such that two or more electrodes are opposing and two or more electrodes are beside one another. The sensor is read by a reader monitoring changes to the sensor due to the presence of the sample. The reader measures the presence and/or concentration of one or more analytes within the sample based upon data obtained by the reader.

20 Claims, 3 Drawing Sheets

(58) Field of Classification Search
CPC ........... G01N 33/5438; G01N 27/3274; G01N 27/3271; G01N 27/403; G01N 27/4145; G01N 33/66; G01N 27/4148; G01N 33/48707; G01N 27/30; G01N 21/76; G01N 33/48785; G01N 15/0656; G01N 27/26
See application file for complete search history.

(56) References Cited

U.S. PATENT DOCUMENTS

| | | | | |
|---|---|---|---|---|
| 5,200,051 | A * | 4/1993 | Cozzette | G01V 9/00 422/930 |
| 5,212,050 | A * | 5/1993 | Mier | C12Q 1/001 430/326 |
| 5,520,787 | A | 5/1996 | Hanagan et al. | |
| 5,814,376 | A * | 9/1998 | Cabelli | C12Q 1/002 427/428.21 |
| 5,837,454 | A * | 11/1998 | Cozzette | C12Q 1/001 435/14 |
| 6,123,820 | A * | 9/2000 | Bergkuist | G01N 33/4915 204/411 |
| 6,212,417 | B1 * | 4/2001 | Ikeda | G01N 27/3272 600/347 |
| 6,544,393 | B1 * | 4/2003 | Kunnecke | G01N 27/403 204/403.01 |
| 6,673,533 | B1 * | 1/2004 | Wohlstadter | B01L 3/5027 436/806 |
| 6,878,251 | B2 * | 4/2005 | Hodges | G01N 27/3272 204/418 |
| 7,074,610 | B2 * | 7/2006 | Cozzette | C12Q 1/001 422/417 |
| 7,824,925 | B2 * | 11/2010 | Wohlstadter | G01N 21/76 436/805 |
| 7,867,369 | B2 | 1/2011 | Bhullar et al. | |
| 7,906,009 | B2 * | 3/2011 | Heller | A61B 5/15113 204/403.02 |
| 8,075,760 | B2 * | 12/2011 | Hodges | G01N 27/403 205/792 |
| 10,378,103 | B2 * | 8/2019 | Jin | G01N 27/3278 |
| 10,422,797 | B2 * | 9/2019 | Kraus | G01N 33/582 |
| 10,718,733 | B2 * | 7/2020 | Milgrew | G01N 27/27 |
| 10,746,724 | B2 * | 8/2020 | Samproni | G01N 33/492 |
| 11,339,430 | B2 * | 5/2022 | Rothberg | H01L 24/18 |
| 2004/0084306 | A1 * | 5/2004 | Shin | G01N 27/27 204/403.01 |
| 2005/0269214 | A1 * | 12/2005 | Lee | G01N 27/3272 204/403.01 |
| 2007/0042450 | A1 | 2/2007 | McGimpsey et al. | |
| 2008/0100279 | A1 * | 5/2008 | Mohapatra | C12Q 1/32 977/762 |
| 2010/0096276 | A1 * | 4/2010 | Kojima | C12Q 1/006 204/403.14 |
| 2014/0105788 | A1 * | 4/2014 | Iwamoto | G01N 27/27 422/82.02 |
| 2014/0273187 | A1 * | 9/2014 | Johnson | G01N 33/5438 435/287.2 |
| 2016/0054257 | A1 * | 2/2016 | Ishige | G01N 27/021 205/789 |
| 2016/0334358 | A1 * | 11/2016 | Kishioka | G01N 27/333 |
| 2017/0010259 | A1 * | 1/2017 | Amoabediny | B01L 3/502 |
| 2017/0015971 | A1 * | 1/2017 | Shunori | G01N 27/403 |
| 2017/0184532 | A1 * | 6/2017 | Samproni | G01N 27/27 |
| 2017/0248622 | A1 * | 8/2017 | Khattak | G01N 35/0098 |
| 2018/0126381 | A1 | 5/2018 | Huff et al. | |
| 2018/0180566 | A1 * | 6/2018 | Nakazato | G01N 27/403 |
| 2019/0008003 | A1 * | 1/2019 | Samproni | G01N 33/48707 |
| 2019/0033252 | A1 * | 1/2019 | Huang | G01N 27/4145 |
| 2019/0195819 | A1 * | 6/2019 | Libsch | G01N 27/00 |
| 2022/0196584 | A1 * | 6/2022 | Lutz | G01N 27/27 |
| 2022/0196632 | A1 * | 6/2022 | Boehm | A61B 5/1468 |
| 2023/0408510 | A1 * | 12/2023 | Goldsmith | G01N 27/4145 |

FOREIGN PATENT DOCUMENTS

| | | | |
|---|---|---|---|
| CN | 101563607 A | 10/2009 | |
| CN | 103069001 A | 4/2013 | |
| CN | 104825171 A | 8/2015 | |
| CN | 111316072 B * | 12/2021 | ............ G01N 21/17 |
| EP | 0984069 A2 | 3/2000 | |
| EP | 1182456 A2 | 2/2002 | |
| EP | 2711415 A2 * | 3/2014 | ......... B01J 19/0046 |
| EP | 2778668 A1 | 9/2014 | |
| JP | S6224141 A | 2/1987 | |
| JP | H7-65978 B | 4/1994 | |
| JP | H09509485 A | 9/1997 | |
| JP | H11505606 A | 5/1999 | |
| JP | H11352093 A | 12/1999 | |
| JP | 2000065778 A | 3/2000 | |
| JP | 2002174610 A | 6/2002 | |
| JP | 2012068235 A | 4/2012 | |
| JP | 2017053808 A | 3/2017 | |
| TW | 201219776 A | 5/2012 | |
| WO | 9522051 A1 | 8/1995 | |
| WO | 2008044530 A1 | 4/2008 | |
| WO | 2009042631 A2 | 4/2009 | |
| WO | 2016011308 A1 | 1/2016 | |
| WO | 2016034696 A1 | 3/2016 | |
| WO | 2016092803 A1 | 6/2016 | |
| WO | 2016106320 A2 | 6/2016 | |
| WO | 2017027477 A1 | 2/2017 | |

OTHER PUBLICATIONS

European Search Report and Search Opinion of European Application No. 18879086.9 dated Dec. 18, 2020.
Collins et al., "Multifrequency spectrum analysis using fully digital G-Mode Kelvin probe force microscopy", Year: Mar. 11, 2016, pp. 1-21.
Liang et al., "Recent Advances in Electrochemical Biosensors for In Vitro Diagnostic", Progress in Chemistry; Year: Dec. 24, 2016, vol. 28, No. 12, pp. 1824-1833.

* cited by examiner

SENSOR ASSEMBLY AND METHOD OF USING SAME

The subject application claims benefit under 35 USC § 119(e) of U.S. provisional Application No. 62/587,856, filed Nov. 17, 2017. The entire contents of the above-referenced patent application are hereby expressly incorporated herein by reference.

BACKGROUND OF THE INVENTION

The present disclosure relates to a sensing device which allows for multiple tests to be run concurrently using a small sample volume.

SUMMARY OF THE DISCLOSURE

In one embodiment, the present disclosure describes a method in which a sample is passed through a fluid flow path of a sensor assembly such that the sample intersects at least one sensor comprising at least three electrodes arranged such that two or more electrodes are opposing and two or more electrodes are beside one another. The sensor is read by a reader monitoring changes to the sensor in the presence of the sample. The reader measures the presence and/or concentration of one or more analytes within the sample based upon data obtained by the reader.

In other embodiments, the present disclosure describes a sensor assembly provided with a first substrate, and a second substrate. The first substrate comprises a first base layer, and a first electrical contact, the first base layer having a first surface and a second surface, a first sensor portion on the first surface and connected to the first electrical contact. The second substrate comprises a second base layer, a second sensor portion, and a plurality of second electrical contacts, the second base layer having a first surface and a second surface with the second sensor portion on the first surface of the second base layer. The first substrate and the second substrate are arranged in a layered structure in which the first surface of the first base layer and the first surface of the second base layer border a fluid flow path intersecting the first sensor portion and the second sensor portion, the first sensor portion aligned with the second sensor portion across the fluid flow path to form an electrochemical type of sensor. The second sensor portion includes a first electrode and a second electrode with the first electrode electrically isolated from the second electrode.

In yet another embodiment, the present disclosure describes a sensor assembly provided with a first substrate and a second substrate. The first substrate comprises a first base layer, the first base layer having a first surface and a second surface, two spaced apart first sensor portions on the first surface. The second substrate comprises a second base layer, the second base layer having a first surface and a second surface, two spaced apart second sensor portions on the first surface. The first substrate and the second substrate are arranged in a layered structure in which the first surface of the first base layer and the first surface of the second base layer border a fluid flow path, one of the first sensor portions is aligned with one of the the second sensor portions across the fluid flow path to form a first sensor, and the other one of the first sensor portions is aligned with the other one of the second sensor portions across the fluid flow path to form a second sensor. Each of the second sensor portions includes a first recognition element and a second recognition element.

In some embodiments, the first recognition element and the second recognition element are electrodes.

Additional features and advantages of the disclosure will be made apparent from the following detailed description of illustrative embodiments that proceeds with reference to the accompanying drawings.

BRIEF DESCRIPTION OF THE DRAWINGS

A more complete appreciation of the present disclosure and many of the attendant advantages thereof will be readily understood by reference to the following detailed description when taken in conjunction with the accompanying drawings, in which.

DESCRIPTION OF THE PREFERRED EMBODIMENTS

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts disclosed and claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts within the instant disclosure may be practiced without these specific details. In other instances, well-known features have not been described in detail to avoid unnecessarily complicating the instant disclosure.

As used herein, the terms "comprises," "comprising," "includes," "including," "has," "having" or any other variation thereof, are intended to cover a non-exclusive inclusion. For example, a composition, a process, method, article, or apparatus that comprises a list of elements is not necessarily limited to only those elements but may include other elements not expressly listed or inherently present therein.

As used herein the terms "approximately," "about," "substantially" and variations thereof are intended to include not only the exact value qualified by the term, but to also include some slight deviations therefrom, such as deviations caused by measuring error, manufacturing tolerances, wear and tear on components or structures, settling or precipitation of cells or particles out of suspension or solution, chemical or biological degradation of solutions over time, stress exerted on structures, and combinations thereof, for example.

As used herein, the term "sample" and variations thereof is intended to include biological tissues, biological fluids, chemical fluids, chemical substances, suspensions, solutions, slurries, mixtures, agglomerations, tinctures, slides, powders, or other preparations of biological tissues or fluids, synthetic analogs to biological tissues or fluids, bacterial cells (prokaryotic or eukaryotic), viruses, singlecelled organisms, lysed biological cells, fixed biological cells, fixed biological tissues, cell cultures, tissue cultures, genetically engineered cells and tissues, genetically engineered organisms, and combinations thereof, for example. The sample can be in a liquid or a gaseous form.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present). An inclusive or may be understood as being the equivalent to: at least one of condition A or B.

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

The inventive concepts disclosed herein are generally directed to the need to minimize the sample volume required to test two or more analytes concurrently. Low sample volumes are desirable when the sample is limited, such as in the case of neonatal patients, or when the sample itself is expensive. As opposed to prior art configurations, which required the volume to increase with the number of analytes being detected, the required sample volume can be greatly reduced when recognition elements of the sensors are arranged in a combination in which two or more recognition elements are facing one another in a sandwich configuration (also referred to as an opposing sensor array) and two or more recognition elements are in a non-opposing configuration which is also referred to herein as a side-by-side configuration or a coplanar configuration. Illustrative opposing and co-planar sensor arrays are discussed in connection with FIGS. 1-4 below.

Figure 1:
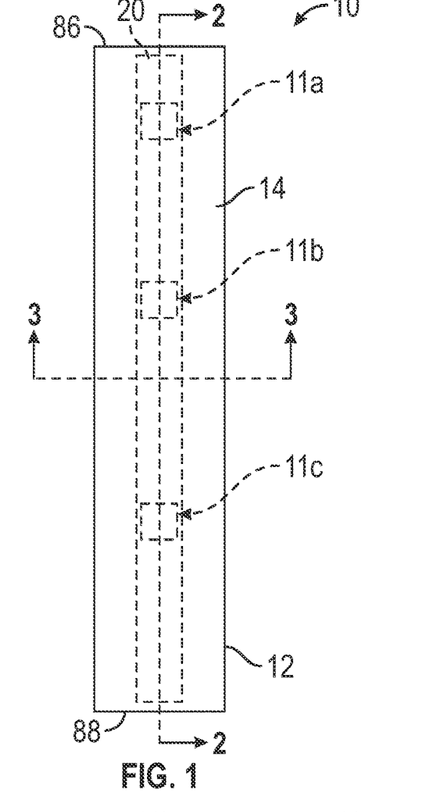
FIG. 1 is a top plan view of one embodiment of an exemplary sensor assembly constructed in accordance with the present disclosure.
Figure 2:
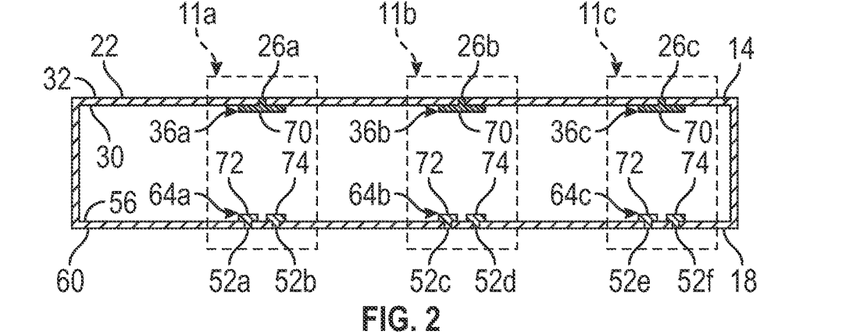
FIG. 2 is a cross-sectional diagram of the sensor assembly of FIG. 1, taken along the lines 2-2.
Figure 3:
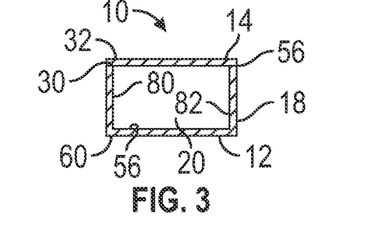
FIG. 3 is a cross-sectional diagram of the sensor assembly of FIG. 1, taken along the lines 3-3.

Referring now to the drawings, and in particular to FIG. 1, shown therein and designated by reference numeral 10 is one embodiment of a sensor assembly constructed in accordance with the present disclosure. FIG. 2 is a cross-sectional view of the sensor assembly 10 taken along the lines 2-2, and FIG. 3 is another cross-sectional diagram of the sensor assembly 10 taken along the lines 3-3 depicted in FIG. 1. As will be discussed below, the sensor assembly 10 includes a plurality of sensors 11 positioned within a housing 12. In FIG. 1, three sensors 11 are shown and designated by reference numerals 11a, 11b and 11c by way of example. It should be understood that the sensor assembly 10 may be provided with more or less of the sensors 11. The sensors 11 can be configured to identify the same analyte of interest or different analytes of interest. For example, the sensor 11a can be configured to detect an electrolyte, the sensor 11b can be configured to detect glucose, and the sensor 11c can be configured to detect neonatal total bilirubin (nBili).

In general, the sensor assembly 10 is provided with a first substrate 14, and a second substrate 18, which collectively form the housing 12. In one embodiment, the first substrate 14 and the second substrate 18 are shaped so as to form a fluid flow path 20 in which the sensors 11a-c are disposed. As will be described below, the sensors 11 are formed of multiple electrodes that are spaced apart and electrically isolated from one another. The sensors 11 may be used to identify and/or measure analytes of interest in the analysis of clinical chemicals such as blood gases, electrolytes, metabolites, DNA and antibodies, including basic and applied research. Each of the sensors 11 is capable of providing specific quantitative or semi-quantitative analytical information using a biological recognition element (biochemical receptor).

The sensors 11 may be classified according to the biological specificity-conferring mechanism or, alternatively, the mode of physicochemical signal transduction. The biological recognition element may be based on a chemical reaction catalysed by, or on an equilibrium reaction with, macromolecules that have been isolated, engineered or present in their original biological environment. In the latter case, equilibrium is generally reached and there is no further, if any, net consumption of analyte(s) by the immobilized biocomplexing agent incorporated into the sensor 11. The sensors 11 may be further classified according to the analytes or reactions that they monitor: direct monitoring of analyte concentration or of reactions producing or consuming such analytes; alternatively, an indirect monitoring of inhibitor or activator of the biological recognition element (biochemical receptor) may be achieved.

The sensors 11 may be of various types. For example, the sensors 11 may be selected from the group comprising an electrochemical sensor, an amperometric sensor, a blood glucose sensor, a potentiometric sensor, a conduct metric sensor, a thermometric sensor, an optical sensor, a fiber optic lactate sensor, a piezoelectric sensor, an immuno-sensor or the like. In certain instances, the sensors 11 may be disposable after one measurement, i.e., single use, and unable to monitor and analyte concentration continuously or at multiple instances of time. In other instances, the sensors 11 may be multi-use in which the sensors 11 are adapted to monitor an analyte concentration continuously or at multiple instances of time. The sensors 11 described herein are integrated devices utilized for detecting analytes of interest, and can be distinguished from an analytical system which incorporates additional separation steps such as high-performance liquid chromatography, or additional hardware and/or sample processing such as specific reagent introduction to identify an analyte of interest. In certain embodiments, the sensors 11 are reagentless analytical devices.

The sensors 11 will be described herein by way of example as an electrochemical type of sensor. It should be understood, however, that the skilled artisan will understand how to create other types of sensors 11 based upon the teachings within the present disclosure.

The electrochemical type of sensor 11 is capable of providing specific quantitative or semi-quantitative analytical information using a biological recognition element (biochemical receptor) which is retained in direct spatial contact with an electrochemical transduction element. The electrochemical type of sensor 11 may be based upon the principle of a transfer of charge from an electrode to another electrode based upon an oxidation or reduction process. During this process, chemical changes take place at the electrodes and the charge is conducted through the sample. By measuring the transfer of charge, a determination of the presence and/or the amounts of analytes of interest may be made. Electrochemical types of sensors 11 may be based upon several principles, such as potentiometric, amperometric, or conductivity measurements. Also, the electrochemical type of sensors 11 may have the ability to be repeatedly calibrated without any reagent addition.

As will be discussed below, the electrochemical type of sensor 11 is provided with at least three recognition elements in the form of electrodes, that may be classified as a working electrode, a counter electrode, and a reference electrode. When the electrochemical type of sensor 11 is based upon potentiometric principles, a voltage potential difference between certain of the electrodes (e.g., a working electrode and a counter electrode) forming the electrochemical type of sensor 11 is read and interpreted. When the electrochemical type of sensor 11 is based upon amperometric principles, a current that is dependent upon the concentration of an analyte is read and interpreted. In some instances, the amount of the current is linearly dependent upon the concentration of analyte. Conductometric sensors are based on the measurement of electrolyte conductivity, which varies when the sensor is exposed to different environments. The electrodes of the electrochemical type of sensor 11, in general, are fabricated of predetermined materials, dopings and/or coatings to provide analyte selectivity to the electrochemical type of sensor 11. For example, the biological receptors, i.e. enzymes, antibodies, cells or tissues, with high biological activity, can be immobilized in a thin layer at the transducer surface by using different procedures, such as entrapment behind a membrane, entrapment within a polymeric matrix, entrapment of biological receptors within self-assembled monolayers or bilayer lipid membranes, covalent bonding of receptors on membranes or surfaces activated by bifunctional groups of spacers, or bulk modification of entire electrode material. Receptors may be immobilized either alone or may be mixed with other proteins, such as bovine serum albumin (BSA), either directly on the electrode, or on a polymer membrane covering the electrode. In the latter case, preactivated membranes can be used directly for the enzyme or antibody immobilization without further chemical modification of the membrane or macromolecule.

In accordance with the present disclosure, the first substrate 14 is provided with a first base layer 22, and a plurality of first electrical contacts 26 (three of the first electrical contacts 26 being depicted in FIG. 2 by way of example and designated by reference numerals 26a, 26b, and 26c). The first base layer 22 may be made from, for example, ceramic, polymer, foil, or any other type of material known to someone of ordinary skill in the art. The first electrical contacts 26 are electrically isolated and may be constructed of an electrically conductive material, such as copper, aluminum, silver, gold, carbon nanotubes, or the like. The first base layer 22 may be provided with a first surface 30, and a second surface 32. The first surface 30 may be a planar surface, i.e., in the form of a plane. In other embodiments, the first surface 30 may be in the form of an arc, or include a combination of planar and arc shaped portions. The first electrical contacts 26 may extend through the first base layer 22 from the first surface 30 to the second surface 32 as shown in FIG. 2 so that a reader (not shown) can be connected to the first electrical contacts 26. In other embodiments, the first electrical contacts 26 may extend across portions of the first surface 30 and/or the second surface 32 so long as the first electrical contacts 26 may be connected to a reader.

Figure 4:
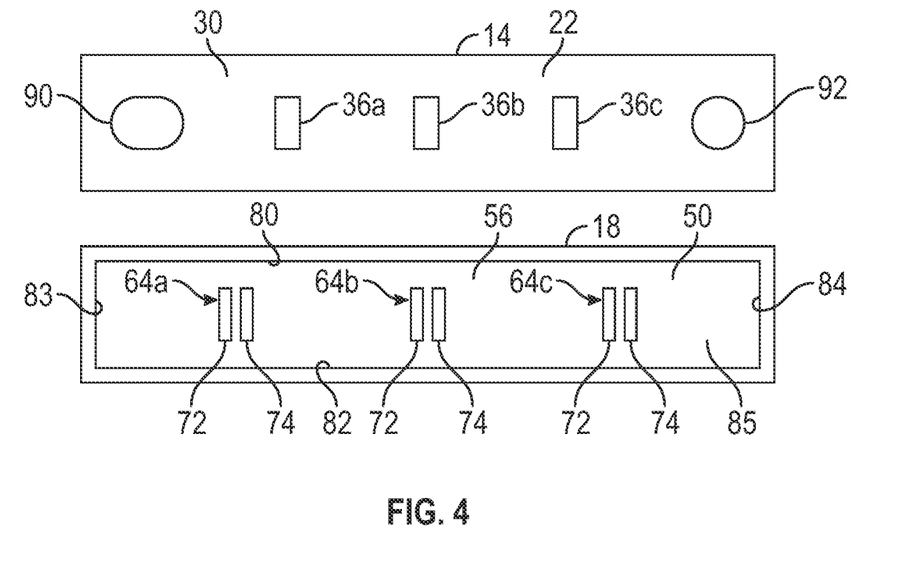
FIG. 4 is a diagrammatic, top plan view of a first substrate and a second substrate utilized to form the sensor assembly depicted in FIG. 1.

The first substrate 14 is also provided with a plurality of first sensor portions 36 connected to and on the first surface 30. The first sensor portions 36 extend over and cover at least a portion of the first surface 30. Although it should be understood that in some embodiments the first sensor portions 36 do not directly contact the first surface 30. Rather, one or more layers of material may be positioned between the first sensor portions 36 and the first surface 30. In addition, in some embodiments, the first surface 30 is devoid of any reaction wells or other areas designed to retain a liquid around the first sensor portions 36. In one embodiment, each of the first sensor portions 36 forms a part of one of the electrochemical sensors 11. By way of example, three of the first sensor portions 36 are depicted and labeled with reference numerals 36a, 36b and 36c. The first sensor portions 36 are spaced apart and electrically isolated from one another. Although the first sensor portions 36 are shown spaced apart in a generally linear arrangement, it should be understood that other arrangements and patterns of the first sensor portions 36 can be used in an effort to maximize the density of the first sensor portions 36. For example, the first sensor portions 36 can be arranged in a staggered arrangement. In the example depicted in FIGS. 2 and 4, the first sensor portion 36a is spaced apart from the first sensor portion 36b and electrically isolated therefrom. Likewise, the first sensor portion 36b is spaced apart from the first sensor portion 36c and electrically isolated therefrom. Although only three of the first sensor portions 36 are depicted, it should be understood that the first substrate 14 can be provided with more or less of the first sensor portions 36. The first sensor portions 36 can be made of an electrically conductive material using any suitable methodology, such as a thick film approach (e.g., screen printing, rotogravure, pad printing, stenciling conductive material such as carbon, Cu, Pt, Pd, Au, and/or Nanotubes, etc) or a thin film approach (e.g., by sputtering, thermal spraying, and/or cold spraying conductive material). While the first sensor portions 36 in FIG. 4 are depicted as being rectangular, it should be understood that this is an exemplary configuration only. The first sensor portions 36 could be constructed in various shapes, such as a line, a circle, a triangle or the like.

Respective ones of the first electrical contacts 26 are connected to the first sensor portions 36. Thus, for example, the first electrical contact 26a is connected to the first sensor portion 36a; the first electrical contact 26b is connected to the first sensor portion 36b; and the first electrical contact 26c is connected to the first sensor portion 36c.

In accordance with the present disclosure, the second substrate 18 is provided with a second base layer 50, and a plurality of second electrical contacts 52 (six of the second electrical contacts 52 being depicted in FIG. 2 by way of example and designated by reference numerals 52a, 52b, 52c, 52d, 52e and 52f). The second base layer 50 may be made from, for example, ceramic, polymer, foil, or any other type of material known to someone of ordinary skill in the art. The second electrical contacts 52 are electrically isolated and may be constructed of an electrically conductive material, such as copper, aluminum, silver, gold, carbon nanotubes, or the like. It should be understood that in some embodiments the first electrical contacts 26 and the second electrical contacts 52 are optional. For instance, the the first electrical contacts 26 and the second electrical contacts 52 may not be included when the sensor 11 is an optical type of sensor that can be read by an optical reader, such as a reflectance meter or a photodetector. The second base layer 50 may be provided with a first surface 56, and a second surface 60. The second electrical contacts 52 may extend through the second base layer 22 from the first surface 56 to the second surface 60 as shown in FIG. 2 so that a reader (not shown) can be connected to the second electrical contacts 26. In other embodiments, the second electrical contacts 52 may extend across portions of the first surface 56 and/or the second surface 60 so long as the second electrical contacts 52 may be connected to a reader.

The second substrate 18 is also provided with a plurality of second sensor portions 64 on the first surface 56. The second sensor portions 64 extend over and cover at least a portion of the first surface 56. Although it should be understood that in some embodiments the second sensor portions 56 do not directly contact the first surface 56. Rather, one or more layers of material may be positioned between the second sensor portions 36 and the first surface 56. In addition, in some embodiments, the first surface 56 is devoid of any reaction wells or other areas designed to retain a liquid around the second sensor portions 64. Although it should be understood that the first surface 36 can be shaped to form one or more reaction wells encompassing respective ones of the second sensor portions. In one embodiment, a combination of the first and second sensor portions 64 forms one of the electrochemical sensors 11. By way of example, three of the second sensor portions 64 are depicted and labeled with reference numerals 64a, 64b and 64c. The second sensor portions 64 are spaced apart and electrically isolated from one another. Although the second sensor portions 64 are shown spaced apart in a generally linear arrangement, it should be understood that other arrangements and patterns of the second sensor portions 64 can be used in an effort to maximize the density of the second sensor portions 64 on the first surface 56. For example, the second sensor portions 64 can be arranged in a staggered arrangement. In the example shown, the second sensor portion 64a is spaced apart from the second sensor portion 64b and electrically isolated therefrom. Likewise, the second sensor portion 64b is spaced apart from the second sensor portion 64c and electrically isolated therefrom. Although only three of the second sensor portions 64 are depicted, it should be understood that the second substrate 18 can be provided with more or less of the second sensor portions 64. The second sensor portions 64 can be made of an electrically conductive material using any suitable methodology, such as a thick film approach (e.g., screen printing, rotogravure, pad printing, stenciling conductive material such as carbon, Cu, Pt, Pd, Au, and/or Nanotubes, etc. . . . ) or a thin film approach (e.g., by sputtering, thermal spraying, and/or cold spraying conductive material).

When the sensor assembly 10 is assembled, the first substrate 14 and the second substrate 18 are arranged in a layered structure in which the first surface 30 of the first base layer 22 extends over and covers the first surface 56 of the second base layer 50. The first surface 30 of the first base layer 22 and the first surface 56 of the second base layer 50 also border the fluid flow path 20. The first substrate 14 can be bonded to the second substrate 18 in a variety of manners, such as using a cohesive, an adhesive, pressure sensitive adhesive, ultraviolet adhesive, thermal adhesive, ultrasonic welding, thermal tacking procedures, or mechanical coupling (e.g., tongue and groove construction). When the first substrate 14 and the second substrate 18 are bonded, the first sensor portions 36 are aligned with the second sensor portions 64 and spaced apart there from so that the sample can flow between the first sensor portions 36 and the second sensor portion 64. In some embodiments, the first sensor portion 36 can be characterized as a single electrode 70. The first sensor portion 36 and the second sensor portion 64 of each electrochemical type of sensor 11 is spaced apart vertically an amount sufficient to electrically isolate the first sensor portion 36 from the second sensor portion 64 in the absence of a sample contacting the first sensor portion 36 and the second sensor portion 64, while permitting the first sensor portion 36 and the second sensor portion 64 to work together to identify an analyte of interest in the presence of the sample. To prevent interference between the electrochemical type of sensors 11, the electrochemical type of sensors 11 are spaced laterally from one another the amount of spacing can be determined based upon the types of sensors 11, the types of samples anticipated to be analyzed, and a desired useful life of the sensor. For example, when the sensors 11 will be used for identifying analytes of interest in blood, and have a desired useful life of 30 days, then a 1 mm spacing between sensors 11 can be used. If a shorter useful life is desired, then the sensors 11 can be spaced closer together.

The second sensor portions 64 are provided with two or more electrodes. In FIG. 2, the second sensor portions 64 include a first electrode 72 and a second electrode 74 with the first electrode 72 electrically isolated from the second electrode 74 in the absence of a sample contacting the first electrode 72 and the second electrode 74. The first electrode 72 and the second electrode 74 are spaced apart a sufficient distance to maintain electrical isolation in the absence of a sample contacting the first electrode 72 and the second electrode 74, while establishing fluidic contact in the presence of the sample to permit the first and second electrodes 72 and 74 to work together to assist in identifying the analyte of interest. The spacing between the first electrode 72 and the second electrode 74 can vary depending upon a type of dielectric between the first electrode 72 and the second electrode 74, as well as a type of sample anticipated to be used with the first electrode 72 and the second electrode 74. In this example, each of the electrochemical type of sensors 11 include a single electrode 70 residing on the first surface 30 of the first base layer 22, and the first electrode 72, and the second electrode 74 residing on the first surface 56 of the second base layer 50.

While the first and second electrodes 72 and 74 in FIG. 4 are depicted as being rectangular, it should be understood that this is an exemplary configuration only. The first and second electrodes 72 and 74 of the second sensor portions 64 could be constructed in various shapes, such as a line, a circle, an arc shape, a triangle or the like. In FIG. 2, the first surface 56 of the second base layer 50 is a planar surface. In this example, the first and second electrodes 72 and 74 are arranged in a co-planar configuration. Thus, the electrodes 70, 72 and 74 of the electrochemical type of sensors 11 are arranged in a combination in which two or more electrodes (e.g., the electrodes 70 and 74) are connected to different support structures (in this case the electrode 70 is connected to the first substrate 14 and the electrode 74 is connected to the second substrate 18) and face one another in a sandwich configuration (also referred to as an opposing sensor array) across the fluid flow path 20, and two or more electrodes (e.g., the electrodes 72 and 74) are connected to a same surface of a support structure (in this example the first surface 56 of the second substrate 18) in a coplanar configuration. In one embodiment, the electrode 70 can be a reference electrode, the electrode 72 can be a working electrode, and the electrode 74 can be a counter electrode. In other embodiments, one or more of the electrochemical sensors 11 could also have an inactive working electrode. In this instance, the inactive working electrode would be a part of the second sensor portion 64.

Respective ones of the second electrical contacts 52 are connected to the second sensor portions 64. Thus, for example, the second electrical contact 52a is connected to the electrode 72 of the electrochemical type of sensor 11a; the second electrical contact 52b is connected to the electrode 74 of of the electrochemical type of sensor 11a; the second electrical contact 52c is connected to the electrode 72 of the electrochemical type of sensor 11a; the second electrical contact 52d is connected to the electrode 74 of the electrochemical type of sensor 11b; the second electrical contact 52e is connected to the electrode 72 of the electrochemical type of sensor 11c; and the second electrical contact 52f is connected to the electrode 74 of the electrochemical type of sensor 11c.

As shown in FIGS. 3 and 4, the second substrate 18 may also be provided with two spaced apart side walls 80, 82, and end walls 83, 84 extending between the first surface 30 of the first base layer 22 and the first surface 56 of the second base layer 50 to define the fluid flow path 20. In this embodiment, the first surface 30 of the first base layer 22, the first surface 56 of the second base layer 50, the sidewalls 80, 82, and the end walls 83, 84 border the fluid flow path 20. In the example shown, the sidewalls 80, 82, and the end walls 83, 84 may be integrally formed with the second base layer 50 to form a unitary structure. In other embodiments, the sidewalls 80, 82, and end walls 83, 84 may be applied onto the first surface 30 of the first base layer 22, or the first surface 56 of the second base layer 50. The sidewalls 80, 82, and end walls 83, 84 are designed so as to not interfere with the reactions (e.g., electrochemical reactions) caused by an interaction with the sample and the electrochemical type of sensors 11. In one embodiment, the sidewalls 80, 82, and end walls 83, 84 are either constructed with a dielectric material, or coated with a dielectric material. It should also be understood that the sidewalls 80, 82, and end walls 83, 84 may be integral with or bonded to the first base layer 22. When the sidewalls 80, 82, and end walls 83, 84 are not integral with the first base layer 22 or the second base layer 50, the sidewalls 80, 82, and end walls 83, 84 may be referred to herein as a dielectric layer having an opening 85 (see FIG. 4) forming the fluid flow path 20 and being closed by the first base layer 22 or the second base layer 50.

As shown in FIG. 1, the sensor assembly 10 is also provided with a first end 86 and a second end 88. In the example shown, the fluid flow path 20 extends generally between the first end 86 and the second end 88, but is separate from (i.e., does not intersect) either one of the first end 86 or the second end 88. For example, as shown in FIG. 4, the first base layer 22 may be provided with an inlet 90 and an outlet 92 that intersect the fluid flow path 20 when the first substrate 14 is bonded to the second substrate 18. In this example, the inlet 90 and the outlet 92 extend through the first base layer 22 from the first surface 30 to the second surface 32 to permit a sample to be disposed within the fluid flow path 20 and flow from the inlet 90 to the outlet 92. As will be appreciated by a person skilled in the art, inlet 90 and/or outlet 92 may be formed in a variety of ways. For example, inlet 90 and/or outlet 92 may be openings in the side of the sensor assembly 10, may be ports (e.g., apertures) formed in one or more layers of first and second substrates 14 and 18. In addition, the first and second substrates 14 and 18 can be designed for the fluid flow path 20 to intersect either one or both of the first end 86 or the second end 88. In some embodiments, the first and second substrates 14 and 18 can be designed to provide two or more fluid flow paths 20, e.g., with one or more of the electrochemical sensors 11 in one or more of the fluid flow paths 20.

Figure 5:
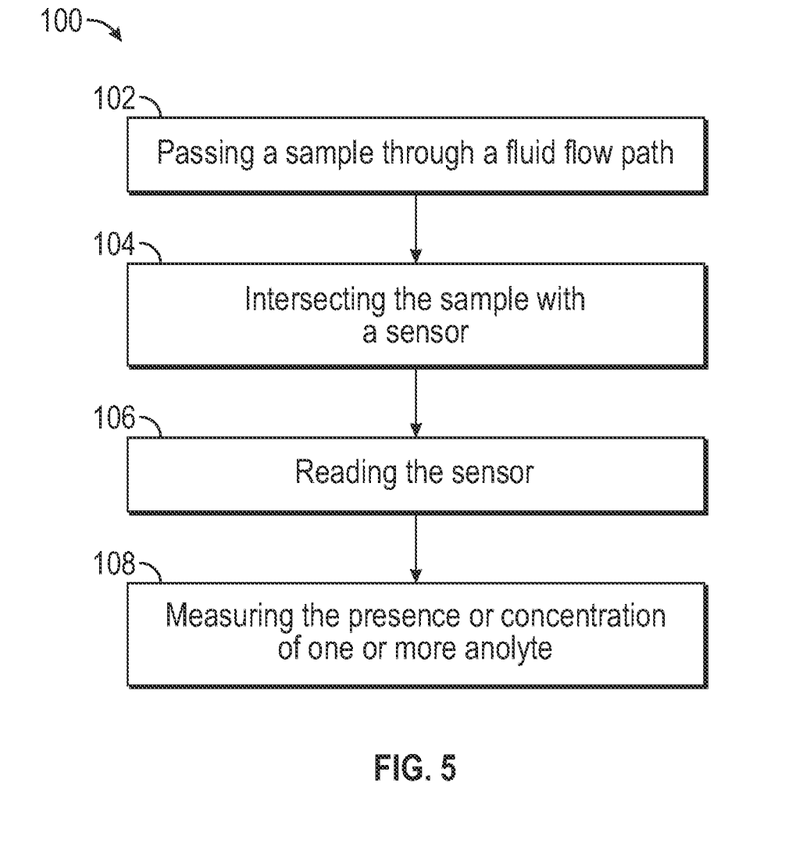
FIG. 5 is a block diagram illustrating a method of using the sensor assembly in accordance with the present disclosure.

FIG. 5 shows a process 100 of measuring the presence and/or concentration of an analyte in accordance with the presently disclosed concepts. In use, the sample is passed through the fluid flow path 20 as indicated by a block 102. This can be accomplished by introducing the sample into the fluid flow path 20 and using a motive force, such as a pump or capilarry action, to move the sample through the fluid flow path 20 to intersect the sensors 11a, 11b or 11c as shown in block 104. As shown in block 106, as the sample intersects the sensors 11 (or a delay from when the sample intersects the sensors 11), the sensors 11 can be read by a reader. For example, the first electrical contacts 26 and the second electrical contacts 52 can be read by a reader when certain ones of the sensors 11 are of the electrochemical type. Or, light emitted from the sensors 11 that are of an optical type (e.g., fluoresce in the presence of an analyte of interest) can be detected by an optical detector, such as a photodetector or a grid of photodetectors. In either case, the reader(s) receive the information (e.g., changes in voltage, amperage, or conductivity, optical signals, or the like), and uses the information to measure the presence and/or concentration of one or more analytes within the sample as indicated by block 108.

While the present disclosure has been described in connection with the exemplary embodiments of the various figures, it is not limited thereto and it is to be understood that other similar embodiments may be used or modifications and additions may be made to the described embodiments for performing the same function of the present disclosure without deviating therefrom.

Figure 6A:
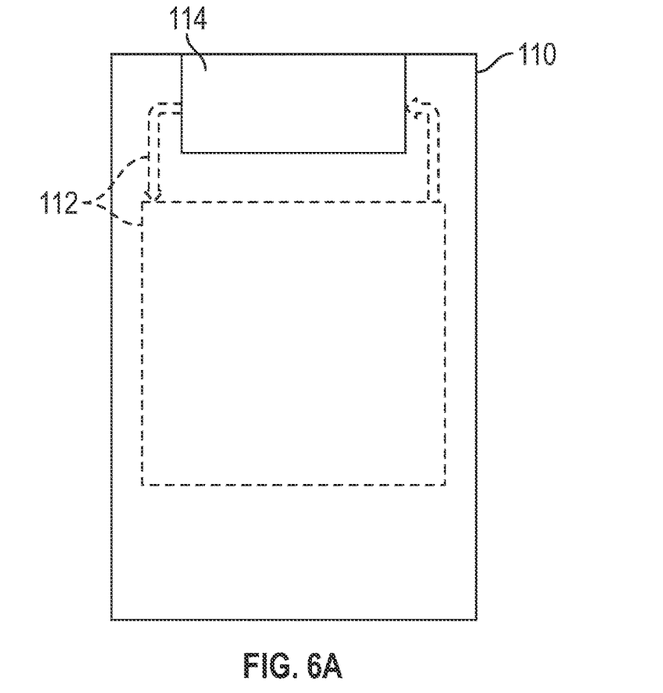
FIGS. 6A and 6B are diagrammatic views of incorporating the sensor assembly into a fluidic housing in accordance with the present disclosure.
Figure 6B:
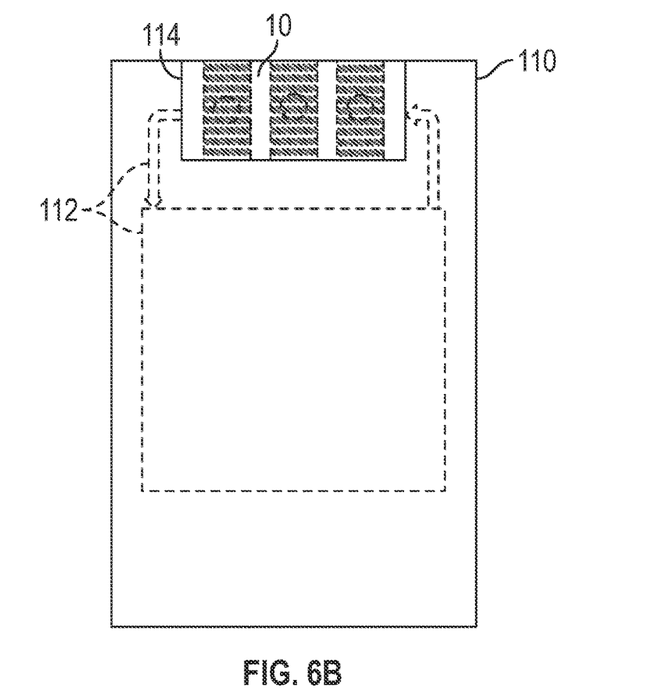

For example, FIGS. 6A and 6B depict an embodiment in which sensor assembly 10 is incorporated into a fluidic housing 110. Fluidic housing 110 may be made of molded plastic and/or polymer and have microfluidic and/or macrofluidic channels 112 incorporated therein (represented by the dashed arrows/box). The sensor assembly 10 can then be inserted into an opening 114 into the housing 110 such that the fluid flow path(s) 20 are placed in fluidic contact with the microfluidic and/or macrofluidic channels 112 such that liquid flows through from the channels 112 into the sensor assembly 10 and back into the channels 112 in the direction of the fluid flow path 20.

Sensor assembly 10 can be bonded to the fluidic housing 110 via, for example, adhesive, ultrasonic welding, thermal sealing, and solvent bonding, etc.

In certain embodiments, the present disclosure describes a method in which a sample is passed through a fluid flow path of a sensor assembly such that the sample intersects at least one sensor comprising at least three electrodes arranged such that two or more electrodes are opposing and two or more electrodes are beside one another. The sensor is read by a reader monitoring changes to the sensor. The reader measures the presence and/or concentration of one or more analytes within the sample based upon data obtained by the reader.

In other embodiments, the present disclosure describes a sensor assembly provided with a first substrate, and a second substrate. The first substrate comprises a first base layer, and a first electrical contact, the first base layer having a first surface and a second surface, a first sensor portion on the first surface and connected to the first electrical contact. The second substrate comprises a second base layer, a second sensor portion, and a plurality of second electrical contacts, the second base layer having a first surface and a second surface with the second sensor portion on the first surface of the second base layer. The first substrate and the second substrate are arranged in a layered structure in which the first surface of the first base layer and the first surface of the second base layer border a fluid flow path intersecting the first sensor portion and the second sensor portion, the first sensor portion aligned with the second sensor portion across the fluid flow path to form an electrochemical type of sensor. The second sensor portion includes a first electrode and a second electrode with the first electrode electrically isolated from the second electrode.

In yet another embodiment, the present disclosure describes a sensor assembly provided with a first substrate and a second substrate. The first substrate comprises a first base layer, the first base layer having a first surface and a second surface, two spaced apart first sensor portions on the first surface. The second substrate comprises a second base layer, the second base layer having a first surface and a second surface, two spaced apart second sensor portions on the first surface. The first substrate and the second substrate are arranged in a layered structure in which the first surface of the first base layer and the first surface of the second base layer border a fluid flow path, one of the first sensor portions is aligned with one of the the second sensor portions across the fluid flow path to form a first sensor, and the other one of the first sensor portions is aligned with the other one of the second sensor portions across the fluid flow path to form a second sensor. Each of the second sensor portions includes a first recognition element and a second recognition element.

In some embodiments, the first recognition element and the second recognition element are electrodes.

Therefore, the present disclosure should not be limited to any single embodiment, but rather should be construed in breadth and scope in accordance with the appended claims. Also, the appended claims should be construed to include other variants and embodiments of the disclosure, which may be made by those skilled in the art without departing from the true spirit and scope of the present disclosure.

What is claimed is:

1. A sensor assembly, comprising:
    a first substrate comprising a first base layer and a plurality of first electrical contacts, the first base layer having a first surface and a second surface, a plurality of first sensor portions constructed of a first electrically conductive material on the first surface and with each of the first sensor portions connected to a respective one of the plurality of first electrical contacts, the first sensor portions spaced apart and electrically isolated; and
    a second substrate comprising a second base layer, a plurality of second sensor portions constructed of a second electrically conductive material, and a plurality of second electrical contacts, the second base layer having a first surface and a second surface with the plurality of second sensor portions on the first surface of the second base layer, the second sensor portions spaced apart and electrically isolated;
    wherein the first substrate and the second substrate are arranged in a layered structure in which the first surface of the first base layer and the first surface of the second base layer border a fluid flow path intersecting the first sensor portions and the second sensor portions, wherein a first one of the first sensor portions is aligned with a first one of the second sensor portions across the fluid flow path to form a first single integrated electrochemical type of sensor where the sensing by the first single integrated electrochemical type of sensor is performed by the first one of the first sensor portions and the first one of the second sensor portions working together to identify a first analyte, and a second one of the first sensor portions is aligned with a second one of the second sensor portions across the fluid flow path to form a second integrated electrochemical type of sensor where the sensing by the second single integrated electrochemical type of sensor is performed by the second one of the first sensor portions and the second one of the second sensor portions working together to identify a second analyte of interest;
    wherein at least one of the second sensor portions includes a first electrode and a second electrode with the first electrode electrically isolated from the second electrode; and
    wherein the first surface of the first base layer and the first surface of the second base layer border the fluid flow path between the first and second electrochemical type of sensors.

2. The sensor assembly of claim 1, wherein the first base layer is constructed of one or more dielectric material, and the second base layer is constructed of one or more dielectric material.

3. The sensor assembly of claim 1, wherein the first base layer includes a conductive layer on the first surface forming the first sensor portions.

4. The sensor assembly of claim 1, wherein the first surface of the first base layer and the first surface of the second base layer are arranged in a parallel relationship.

5. The sensor assembly of claim 1, further comprising two spaced apart side walls extending between the first surface of the first base layer, and the first surface of the second base layer; and the first surface of the first base layer, the first surface of the second base layer, and the side walls bordering the fluid flow path.

6. The sensor assembly of claim 1, further comprising a dielectric layer positioned between the first surface of the first base layer and the first sensor portions.

7. The sensor assembly of claim 1, further comprising a dielectric layer positioned between the first surface of the second base layer and the second sensor portions.

8. The sensor assembly of claim 1, wherein the first sensor portions are reference electrodes, the first electrode is a working electrode and the second electrode is a counter electrode.

9. A sensor assembly, comprising:
    a first substrate comprising a first base layer, the first base layer having a first surface and a second surface, two spaced apart first sensor portions on the first surface; and
    a second substrate comprising a second base layer, the second base layer having a first surface and a second surface, two spaced apart second sensor portions on the first surface,
    wherein the first substrate and the second substrate are arranged in a layered structure in which the first surface of the first base layer and the first surface of the second base layer border a fluid flow path, a first one of the first sensor portions is aligned with a first one of the second sensor portions across the fluid flow path to form a first single integrated sensor and where the sensing by the first single integrated sensor is performed by the first one of the first sensor portions and the first one of the second sensor portions working together to identify a first analyte of interest, and a second one of the first sensor portions is aligned with a second one of the second sensor portions across the fluid flow path to form a second single integrated sensor and where the sensing by the second single integrated sensor is performed by the second one of the first sensor portions and the second one of the second sensor portions working together to identify a second analyte of interest, and wherein each of the second sensor portions include a first recognition element and a second recognition element.

10. The sensor assembly of claim 9, wherein the first base layer is constructed of one or more dielectric material, and the second base layer is constructed of one or more dielectric material.

11. The sensor assembly of claim 9, wherein the first base layer includes a conductive layer on the first surface, the conductive layer being shaped to form the first sensor portions.

12. The sensor assembly of claim 9, wherein the first surface of the first base layer and the first surface of the second base layer are arranged in a parallel relationship.

13. The sensor assembly of claim 9, further comprising two spaced apart side walls extending between the first surface of the first base layer and the first surface of the second base layer, the first surface of the first base layer, the first surface of the second base layer, and the side walls bordering the fluid flow path.

14. A method, comprising:
passing a sample through a fluid flow path at least partially formed by a first surface of a first substrate and a first surface of a second substrate of a sensor assembly such that the sample intersects the first surface of the first substrate and the first surface of the second substrate and intersects a plurality of first sensor portions disposed on the first surface of the first substrate and a plurality of second sensor portions disposed on the first surface of the second substrate, and spatially disposed along the fluid flow path, the fluid flow path being devoid of any reaction wells or other areas designed to retain a liquid around the first sensor portions and the second sensor portions such that the sample is passed through the fluid flow path without being retained around the first sensor portions and the second sensor portions, wherein a first one of the first sensor portions is aligned with a first one of the second sensor portions across the fluid flow path to form a first single integrated sensor, and another one of the first sensor portions is aligned with another one of the second sensor portions across the fluid flow path to form a second single integrated sensor,
wherein sensing by the first single integrated sensor is performed by the first one of the first sensor portions and the first one of the second sensor portions working together to identify a first analyte of interest, and
wherein sensing by the second single integrated sensor is performed by the second one of the first sensor portions and the second one of the second sensor portions working together to identify a second analyte of interest;
reading the first single integrated sensor and the second single integrated sensor by a reader monitoring changes to the first single integrated sensor and the second single integrated sensor; and
measuring the presence and/or concentration of one or more analytes within the sample based upon data obtained by the reader.

15. The method of claim 14, wherein at least one of the first single integrated sensor and the second single integrated sensor is an electrochemical type of sensor having electrical contacts connected to at least three electrodes, and wherein reading the electrochemical type of sensor comprises the reader monitoring the electrical contacts and wherein measuring the presence and/or concentration of one or more analytes within the sample based upon data obtained by the reader from the electrical contacts.

16. The method of claim 15, wherein at least two of the electrodes are beside one another on a first surface of a first substrate, and at least one of the electrodes is on a first surface of a second substrate.

17. The method of claim 14, wherein the first single integrated sensor is of a first type, and the second single integrated sensor is of a second type, wherein the first type is different from the second type.

18. The method of claim 17, wherein the first type of sensor is an electrochemical type of sensor, and the second type of sensor is an optical type of sensor.

19. A sensor assembly, comprising:
a first substrate comprising a first base layer and a plurality of first electrical contacts, the first base layer having a first surface and a second surface, a plurality of first sensor portions constructed of a first electrically conductive material on the first surface and with each of the first sensor portions connected to a respective one of the plurality of first electrical contacts, the first sensor portions spaced apart and electrically isolated; and
a second substrate comprising a second base layer, a plurality of second sensor portions constructed of a first electrically conductive material, and a plurality of second electrical contacts, the second base layer having a first surface and a second surface with the plurality of second sensor portions on the first surface of the second base layer, the second sensor portions spaced apart and electrically isolated;
wherein the first surface of the second substrate is shaped to form a reaction well encompassing the second sensor portion, and wherein the first substrate and the second substrate are arranged in a layered structure in which the first surface of the first base layer and the first surface of the second base layer border a fluid flow path intersecting the first sensor portions and the second sensor portions, wherein a first one of the first sensor portions is aligned with a first one of the second sensor portions across the fluid flow path to form a first single integrated electrochemical type of sensor where the sensing by the first single integrated electrochemical type of sensor is performed by the first one of the first sensor portions and the first one of the second sensor portions working together to identify a first analyte, and a second one of the first sensor portions is aligned with a second one of the second sensor portions across the fluid flow path to form a second single integrated electrochemical type of sensor where the sensing by the second single integrated electrochemical type of sensor is performed by the second one of the first sensor portions and the second one of the second sensor portions working together to identify a second analyte of interest;
wherein at least one of the second sensor portions includes a first electrode and a second electrode with the first electrode electrically isolated from the second electrode; and wherein the first surface of the first base layer and the first surface of the second base layer border the fluid flow path between an adjacent pair of electrochemical type of sensors.

20. A sensor assembly comprising:
a first substrate comprising a first base layer and a plurality of first electrical contacts, the first base layer having a first surface and a second surface with the plurality of first electrical contacts extending through the first substrate from the first surface to the second surface, a plurality of first sensor portions constructed of a first electrically conductive material on the first surface and with each of the first sensor portions connected to a respective one of the plurality of first electrical contacts, the first sensor portions spaced apart and electrically isolated; and
a second substrate comprising a second base layer, a plurality of second sensor portions constructed of a second electrically conductive material, and a plurality of second electrical contacts, the second base layer having a first surface and a second surface with the plurality of second sensor portions on the first surface of the second base layer and the plurality of second electrical contacts extending through the second substrate from the first surface to the second surface, the second sensor portions spaced apart and electrically isolated;
wherein the first substrate and the second substrate are arranged in a layered structure in which the first surface of the first base layer and the first surface of the second base layer border a fluid flow path intersecting the first sensor portions and the second sensor portions, wherein a first one of the first sensor portions is aligned with a first one of the second sensor portions across the fluid flow path to form a first single integrated electrochemical type of sensor where the sensing by the first single integrated electrochemical type of sensor is performed by the first one of the first sensor portions and the first one of the second sensor portions working together to identify a first analyte, and a second one of the first sensor portions is aligned with a second one of the second sensor portions across the fluid flow path to form a second single integrated electrochemical type of sensor where the sensing by the second single integrated electrochemical type of sensor is performed by the second one of the first sensor portions and the second one of the second sensor portions working together to identify a second analyte of interest;
wherein at least one of the second sensor portions includes a first electrode and a second electrode with the first electrode electrically isolated from the second electrode; and
wherein the first surface of the first base layer and the first surface of the second base layer border the fluid flow path between the first and second electrochemical type of sensors.

* * * * *